US010627142B2

(12) United States Patent
Brown et al.

(10) Patent No.: US 10,627,142 B2
(45) Date of Patent: Apr. 21, 2020

(54) APPARATUS AND METHOD FOR DETERMINING THE QUANTITY OF DISSOLVED REFRIGERANT IN OIL RECOVERED FROM AN AIR CONDITIONING SYSTEM

(71) Applicants: Bosch Automotive Service Solutions Inc., Warren, MI (US); Robert Bosch GmbH, Stuttgart (DE)

(72) Inventors: William Brown, Owatonna, MN (US); Mark McMasters, Owatonna, MN (US); Mahendra Hospet Basavapura Srinivasa, Owatonna, MN (US)

(73) Assignees: Bosch Automotive Service Solutions Inc., Warren, MI (US); Robert Bosch GmbH, Stuttgart (DE)

(*) Notice: Subject to any disclaimer, the term of this patent is extended or adjusted under 35 U.S.C. 154(b) by 149 days.

(21) Appl. No.: 15/685,923

(22) Filed: Aug. 24, 2017

(65) Prior Publication Data

US 2018/0120008 A1    May 3, 2018

Related U.S. Application Data

(60) Provisional application No. 62/413,463, filed on Oct. 27, 2016.

(51) Int. Cl.
*F25B 45/00* (2006.01)
*F25B 43/02* (2006.01)
*G01N 33/28* (2006.01)

(52) U.S. Cl.
CPC ............. *F25B 45/00* (2013.01); *F25B 43/02* (2013.01); *F25B 2345/002* (2013.01); *F25B 2345/007* (2013.01); *F25B 2500/19* (2013.01); *G01N 33/2835* (2013.01)

(58) Field of Classification Search
CPC ............................ F25B 45/00; F25B 2500/19; F25B 2345/002; F25B 2345/007; F25B 43/02; G01N 33/2835
USPC ........................................................ 62/149, 77
See application file for complete search history.

(56) References Cited

U.S. PATENT DOCUMENTS

| | | | | | |
|---|---|---|---|---|---|
| 3,873,289 | A | * | 3/1975 | White | B60H 1/00585 62/149 |
| 4,285,206 | A | * | 8/1981 | Koser | B60H 1/00585 62/126 |
| 4,364,236 | A | * | 12/1982 | Lower | B60H 1/00585 62/77 |
| 4,688,388 | A | * | 8/1987 | Lower | B60H 1/00585 62/126 |
| 5,193,351 | A | * | 3/1993 | Laukhuf | F25B 45/00 62/195 |
| 5,369,959 | A | * | 12/1994 | Pfefferle | B60H 1/00585 62/195 |
| 5,479,788 | A | * | 1/1996 | Roegner | F25B 45/00 62/292 |

(Continued)

*Primary Examiner* — Cassey D Bauer
*Assistant Examiner* — Kirstin U Oswald
(74) *Attorney, Agent, or Firm* — Kelly McGlashen; Maginot, Moore & Beck LLP (57) ABSTRACT

An air conditioning service unit and method of using same provide increased accuracy in determining respective amounts of refrigerant and oil recovered during service of an air conditioning system by taking into account the quantity of dissolved refrigerant in oil recovered from the system.

6 Claims, 5 Drawing Sheets

(56) References Cited

U.S. PATENT DOCUMENTS

| | | | | |
|---|---|---|---|---|
| 5,560,215 A * | 10/1996 | Talarico | B60H 1/00585 | 62/149 |
| 5,758,506 A * | 6/1998 | Hancock | B60H 1/00585 | 62/149 |
| 5,802,859 A * | 9/1998 | Zugibe | F25B 45/00 | 62/125 |
| 5,934,091 A * | 8/1999 | Hanson | B60H 1/00585 | 62/149 |
| 6,244,055 B1 * | 6/2001 | Hanson | B60H 1/00585 | 62/149 |
| 8,590,321 B2 * | 11/2013 | McMasters | B60H 1/00585 | 62/149 |
| 2009/0158756 A1 * | 6/2009 | Brown | B60H 1/00585 | 62/77 |
| 2009/0188263 A1 * | 7/2009 | Murray | B60H 1/00585 | 62/77 |
| 2012/0079839 A1 * | 4/2012 | McMasters | B60H 1/00585 | 62/84 |
| 2012/0291457 A1 * | 11/2012 | Brown | F25B 45/00 | 62/77 |
| 2013/0047635 A1 * | 2/2013 | Shultz | F25B 45/00 | 62/77 |
| 2013/0298578 A1 * | 11/2013 | McMasters | F25B 45/00 | 62/77 |
| 2013/0298995 A1 * | 11/2013 | McMasters | F25B 45/00 | 137/1 |
| 2014/0260350 A1 * | 9/2014 | McMasters | F25B 45/00 | 62/77 |
| 2014/0260351 A1 * | 9/2014 | McMasters | F25B 45/00 | 62/77 |
| 2014/0260352 A1 * | 9/2014 | Murray | F25B 45/00 | 62/77 |
| 2014/0260353 A1 * | 9/2014 | Brown | F25B 45/00 | 62/77 |
| 2015/0153083 A1 * | 6/2015 | McMasters | F25B 45/00 | 62/56 |
| 2015/0308722 A1 * | 10/2015 | Lundberg | F25B 45/00 | 62/192 |
| 2016/0123641 A1 * | 5/2016 | McMasters | F25B 45/00 | 62/77 |
| 2016/0123642 A1 * | 5/2016 | Murray | F25B 45/00 | 62/77 |
| 2016/0138843 A1 * | 5/2016 | Lundberg | F25B 45/00 | 62/77 |
| 2016/0169569 A1 * | 6/2016 | Lundberg | F25B 45/00 | 62/77 |
| 2016/0187042 A1 * | 6/2016 | Brown | F25B 45/00 | 62/56 |
| 2017/0045277 A1 * | 2/2017 | McMasters | F25B 45/00 | |

* cited by examiner

APPARATUS AND METHOD FOR DETERMINING THE QUANTITY OF DISSOLVED REFRIGERANT IN OIL RECOVERED FROM AN AIR CONDITIONING SYSTEM

CROSS-REFERENCE TO RELATED APPLICATIONS

This application claims the benefit of U.S. Provisional Patent Application Ser. No. 62/413,463, filed Oct. 27, 2016, the entire content of which is hereby incorporated by reference herein.

BACKGROUND

This disclosure relates generally to refrigerant recovery systems for refrigeration systems, and more particularly to an apparatus and method for providing increased accuracy in determining respective amounts of refrigerant and oil recovered during service of an air conditioning system by taking into account the quantity of dissolved refrigerant in oil recovered from the system.

Air conditioning systems are currently commonplace in homes, office buildings and a variety of vehicles including, for example, automobiles. In order to maintain the overall efficiency and efficacy of an air conditioning system, the refrigerant included therein may be periodically replaced or recharged. Portable carts, also known as recover, recycle, recharge ("RRR") refrigerant service carts or air conditioning service ("ACS") units, are used in connection with servicing refrigeration circuits of air conditioning systems, including retrieving refrigerant from the air conditioning system. The portable machines include hoses coupled to the refrigeration circuit to be serviced.

Some air conditioning systems include a mechanical compressor that requires oil to properly function. During normal operation of the air conditioning system, a portion of the oil from the compressor is entrained in the refrigerant and circulated through the air conditioning system. During servicing of the air conditioning system, the oil entrained refrigerant from the air conditioning system is drained into an ACS unit, where the oil is separated from the refrigerant during a recycling/purification process. The recovered, separated oil is then drained from the ACS unit into a bottle so that it can be determined how much oil needs to be injected back into the air conditioning system. Replacement of an accurate quantity of the oil lost to entrainment with new oil, as well as accurate replacement of the quantity of recovered refrigerant is important to ensure proper and efficient operation of the air conditioning system.

In some conventional service methods, refrigerant dissolved in the oil was not accounted for when measuring the amounts of refrigerant and oil recovered, leading to inaccuracy in the measured amounts, and thus inaccuracy in the amount of oil supplied to the compressor and refrigerant supplied to the system during system service.

It would therefore be desirable to provide an ACS unit having improved accuracy in determining the amount of refrigerant and the amount of oil recovered during service of an air condition system.

SUMMARY

In some aspects, a method of determining an amount of oil in a refrigerant-oil mixture recovered from an air conditioning system includes collecting the refrigerant-oil mixture recovered from the air conditioning system in a receptacle; draining from the receptacle oil that separated from the refrigerant-oil mixture; measuring an amount of the oil drained from the receptacle to obtain a measured amount of recovered oil; and calculating a corrected amount of recovered oil in the refrigerant-oil mixture by correcting the measured amount of recovered oil to account for an amount of dissolved refrigerant in the recovered oil.

The method may include providing an amount of dissolved refrigerant in the recovered oil, including calculating a rate of oil drain by dividing the measured amount of recovered oil by a time required to drain oil from the receptacle; detecting an ambient temperature, and calculating a ratio R of the amount of dissolved refrigerant in the recovered oil to the measured amount of recovered oil, where the ratio R is a function of the rate of oil drain in accordance with the following relationship: $R=a(r-h)^2+k$. In this relationship, r corresponds to the rate of oil drain, and the constants a, h and k are predetermined and depend on the ambient temperature. Providing an amount of dissolved refrigerant in the recovered oil may further include calculating the amount of dissolved refrigerant in the recovered oil by multiplying the value calculated for R by the measured amount of dissolved refrigerant in the recovered oil.

The method may include the following additional steps: prior to draining oil from the receptacle to an oil drain bottle, detecting an initial weight of the oil drain bottle using a load transducer; and detecting an ambient temperature of air conditioning unit using a temperature sensor. The step of draining from the receptacle oil that separated from the refrigerant-oil mixture may include draining the oil into the oil drain bottle while measuring a time required for draining the oil from the receptacle into the oil drain bottle. In addition, the step of measuring an amount of the oil drained from the receptacle may include, following draining of the oil from the receptacle to the oil drain bottle, detecting a final weight of the oil drain bottle using the load transducer, and calculating the measured amount of recovered oil by determining a difference in the final weight of the oil drain bottle and the initial weight of the oil drain bottle.

The method may include the following additional steps: prior to transferring refrigerant from the receptacle to a refrigerant vessel, measuring an initial weight of the refrigerant vessel; transferring from the receptacle to the refrigerant vessel refrigerant that has separated from the refrigerant-oil mixture disposed in the receptacle; measuring an amount of the refrigerant transferred from the receptacle corresponding to a measured amount of recovered refrigerant. This may include detecting a final weight of the refrigerant vessel following transfer of the refrigerant from the receptacle to the refrigerant vessel, calculating the measured amount of recovered refrigerant by determining a difference in the final weight of the refrigerant vessel and the initial weight of the refrigerant vessel. The method may further include calculating a corrected amount of recovered refrigerant by correcting the measured amount of recovered refrigerant to account for an amount of dissolved refrigerant in the recovered oil.

The method may include recharging the air conditioning system with an amount of refrigerant corresponding to the corrected amount of recovered refrigerant.

The method may include recharging the air conditioning system with an amount of oil corresponding to the corrected amount of recovered oil.

In some aspects, a method of determining an amount of oil in a refrigerant-oil mixture recovered from an air conditioning system using an air conditioning service unit includes providing the air conditioning service unit. The air conditioning service unit includes a receptacle configured to receive a refrigerant-oil mixture recovered from the air conditioning system, the receptacle including a drain valve; a refrigerant vessel including a first load transducer configured to detect a weight of the refrigerant vessel; an oil drain bottle including a second load transducer configured to detect a weight of the oil drain bottle; a timer; a temperature sensor configured to detect an ambient temperature of the system; and a controller. The controller is configured to receive as inputs information sent from the temperature sensor, the first load transducer, the second load transducer and the timer. The controller includes a processor configured to execute instructions stored in a memory.

The method of determining an amount of oil in a refrigerant-oil mixture recovered from an air conditioning system using an air conditioning service unit further includes the following method steps: prior to draining oil from the receptacle to the oil drain bottle, detecting an initial weight of the oil drain bottle based on output from the second load transducer; detecting an ambient temperature based on output from the temperature sensor; and draining the oil from the receptacle to the oil drain bottle. The step of draining the oil includes starting the timer and storing a timer start time; opening the drain valve to drain from the receptacle oil that has separated from the refrigerant-oil mixture disposed in the receptacle; detecting if the oil has been drained from the receptacle; and stopping the timer when it has been determined that the oil has been drained from the receptacle and storing a timer stop time. The method of determining an amount of oil in a refrigerant-oil mixture recovered from an air conditioning system using an air conditioning service unit further includes calculating a time required for draining the oil from the receptacle into the oil drain bottle by determining a difference between the timer stop time and the timer start time; following draining oil from the receptacle to the oil drain bottle, detecting a final weight of the oil drain bottle based on output from the second transducer; calculating a difference between the final weight of the oil drain bottle and the initial weight of the oil drain bottle to provide a measured amount of recovered oil corresponding to an amount of the oil drained from the receptacle; and calculating a corrected amount of recovered oil in the refrigerant-oil mixture by correcting the measured amount of recovered oil to account for an amount of dissolved refrigerant in the recovered oil.

The method may include providing an amount of dissolved refrigerant in the recovered oil, including calculating a rate of oil drain by dividing the measured amount of recovered oil by the time required for draining the oil from the receptacle into the oil drain bottle; calculating a ratio of the amount of dissolved refrigerant in the recovered oil to the measured amount of recovered oil based on the rate of oil drain; and calculating the amount of dissolved refrigerant in the recovered oil by multiplying the measured amount of recovered oil by the ratio. The relationship between the ratio and the rate of oil drain is predetermined and based on ambient temperature. In addition, the step of correcting the measured amount of recovered oil to account for an amount of dissolved refrigerant in the recovered oil comprises subtracting the amount of dissolved refrigerant in the recovered oil from the measured amount of recovered oil.

The method may include providing an amount of dissolved refrigerant in the recovered oil, including calculating a rate of oil drain by dividing the measured amount of recovered oil by a time required to drain oil from the receptacle; detecting an ambient temperature; calculating a ratio R of the amount of dissolved refrigerant in the recovered oil to the measured amount of recovered oil, where the ratio R is a function of the rate of oil drain in accordance with the following relationship: $R=a(r-h)^2+k$. In this relationship, r corresponds to the rate of oil drain, and the constants a, h and k are predetermined and depend on the ambient temperature. The method may further include calculating the amount of dissolved refrigerant in the recovered oil by multiplying the value calculated for R by the measured amount of recovered oil, and recharging the air conditioning system with an amount of oil corresponding to the corrected amount of recovered oil.

In some aspects, an air conditioning service unit includes a receptacle configured to receive a refrigerant-oil mixture recovered from an air conditioning system, the receptacle including a drain valve; a refrigerant vessel including a first load transducer configured to determine a weight of the refrigerant vessel; an oil drain bottle including a second load transducer configured to determine a weight of the oil drain bottle; and a timer. The air conditioning service unit also includes a temperature sensor configured to detect an ambient temperature of the system; and a controller configured to receive as inputs information sent from the temperature sensor, the first load transducer, the second load transducer and the timer. The controller includes a processor configured to execute instructions stored in a memory to determine an amount of oil in the refrigerant-oil mixture recovered from the air conditioning unit and collected in the receptacle. The processor may perform the following steps: collecting the refrigerant-oil mixture recovered from the air conditioning system in a receptacle; draining from the receptacle oil that separated from the refrigerant-oil mixture; measuring an amount of the oil drained from the receptacle to obtain a measured amount of recovered oil; and calculating a corrected amount of recovered oil in the refrigerant-oil mixture by correcting the measured amount of recovered oil to account for an amount of dissolved refrigerant in the recovered oil.

The processor may perform the following additional steps to determine an amount of oil in the refrigerant-oil mixture recovered from the air conditioning unit, including: prior to draining oil from the receptacle to the oil drain bottle, detecting an initial weight of the oil drain bottle based on output from the second transducer; detecting an ambient temperature based on output from the temperature sensor; and draining the oil from the receptacle to the oil drain bottle. The step of draining the oil may include starting the timer and storing a timer start time; opening the drain valve to drain from the receptacle oil that has separated from the refrigerant-oil mixture disposed in the receptacle; detecting if the oil has been drained from the receptacle; and stopping the timer when it has been determined that the oil has been drained from the receptacle and storing a timer stop time. The processor may further calculate a time required for draining the oil from the receptacle into the oil drain bottle by determining a difference between the timer stop time and the timer start time; following transferring oil from the receptacle to the oil drain bottle, detect a final weight of the oil drain bottle based on output from the second transducer; calculate a difference between the final weight of the oil drain bottle and the initial weight of the oil drain bottle to provide a measured amount of recovered oil; calculate an amount of dissolved refrigerant in the recovered oil, and calculate a corrected amount of oil in the refrigerant-oil mixture by correcting the measured amount of recovered oil to account for the amount of dissolved refrigerant in the recovered oil.

The processor may perform the following additional steps to determine an amount of oil in the refrigerant-oil mixture recovered from the air conditioning unit, including: calculating a rate of oil drain by dividing the measured amount of recovered oil by a time required to drain oil from the receptacle; detecting an ambient temperature; and calculating a ratio R of the amount of dissolved refrigerant in the recovered oil to the measured amount of recovered oil, where the ratio R is a function of the rate of oil drain in accordance with the following relationship: $R=a(r-h)^2+k$. In this relationship, r corresponds to the rate of oil drain, and the constants a, h and k are predetermined and depend on the ambient temperature. The processor further performs the step of calculating the amount of dissolved refrigerant in the recovered oil by multiplying the value calculated for R by the measured amount of recovered oil.

The processor may be configured to execute instructions stored in a memory to determine an amount of refrigerant in the refrigerant-oil mixture recovered from the air conditioning unit and collected in the receptacle, by performing the following method steps: prior to transferring refrigerant from the receptacle to the refrigerant vessel, detecting an initial weight of the refrigerant vessel based on output from the first load transducer; transferring from the receptacle to the refrigerant vessel refrigerant separated from the refrigerant-oil mixture disposed in the receptacle; following transfer of refrigerant from the receptacle to the refrigerant vessel, detecting a final weight of the refrigerant vessel based on output from the first load transducer; calculating a difference between the final weight of the refrigerant vessel and the initial weight of the refrigerant vessel to provide a measured amount of recovered refrigerant corresponding to an amount of the refrigerant transferred from the receptacle; and calculating a corrected amount of recovered refrigerant by correcting the measured amount of recovered refrigerant to account for an amount of dissolved refrigerant in the recovered oil.

The processor may be configured to execute instructions stored in a memory to recharge an air conditioning system with an amount of refrigerant corresponding to the corrected amount of recovered refrigerant.

The processor may be configured to execute instructions stored in a memory to recharge an air conditioning system with an amount of oil corresponding to the corrected amount of recovered oil.

In some aspects, a method of determining an amount of oil in a refrigerant-oil mixture recovered from an air conditioning system is provided. The method includes placing the refrigerant-oil mixture recovered from the air conditioning unit in a receptacle; draining from the receptacle oil that separated from the refrigerant-oil mixture; and measuring an amount of recovered oil corresponding to an amount of the oil drained from the receptacle. The method also includes correcting the measured amount of oil in the refrigerant-oil mixture to account for an amount of refrigerant that is dissolved in the measured amount of recovered oil. The amount of refrigerant that is dissolved in the measured amount of recovered oil is determined by calculating a rate of oil drain by dividing the measured amount of recovered oil by a time required to drain oil from the receptacle and determining an ambient temperature. In addition, a ratio R of the amount of dissolved refrigerant in the recovered oil to the measured amount of recovered oil is determined. The ratio R is a function of the rate of oil drain in accordance with the following relationship: $R=a(r-h)^2+k$. In this relationship, the value of r corresponds to the rate of oil drain, and the constants a, h and k are predetermined and depend on the ambient temperature. The method further includes calculating the amount of dissolved refrigerant in the recovered oil by multiplying the value obtained for R by the measured amount of dissolved refrigerant in the recovered oil.

In addition, the method includes correcting the measured amount of recovered oil to account for an amount of dissolved refrigerant in the recovered oil. The amount of recovered refrigerant can also be corrected to account for an amount of dissolved refrigerant in the recovered oil. By doing so, the amounts of refrigerant and oil recovered from an air conditioning system during servicing can be more accurately determined, and this information can be used to ensure that proper amounts of refrigerant and oil are used when recharging the air conditioning system.

The method described herein provides a more accurate determination of the amount of recovered refrigerant and the amount of recovered oil from the air conditioning system than some conventional ACS units that do not account for the amount of refrigerant dissolved in the entrained oil. Moreover, by increasing the accuracy of determination of the amount of refrigerant recovered and the amount of oil recovered from the air conditioning system, the service performed on the air conditioning system is more precise, and durability of the air conditioning system including the compressor is improved.

DETAILED DESCRIPTION

For the purposes of promoting an understanding of the principles of the embodiments described herein, reference is now made to the drawings and descriptions in the following written specification. No limitation to the scope of the subject matter is intended by the references. This disclosure also includes any alterations and modifications to the illustrated embodiments and includes further applications of the principles of the described embodiments as would normally occur to one skilled in the art to which this document pertains.

Figure 1:
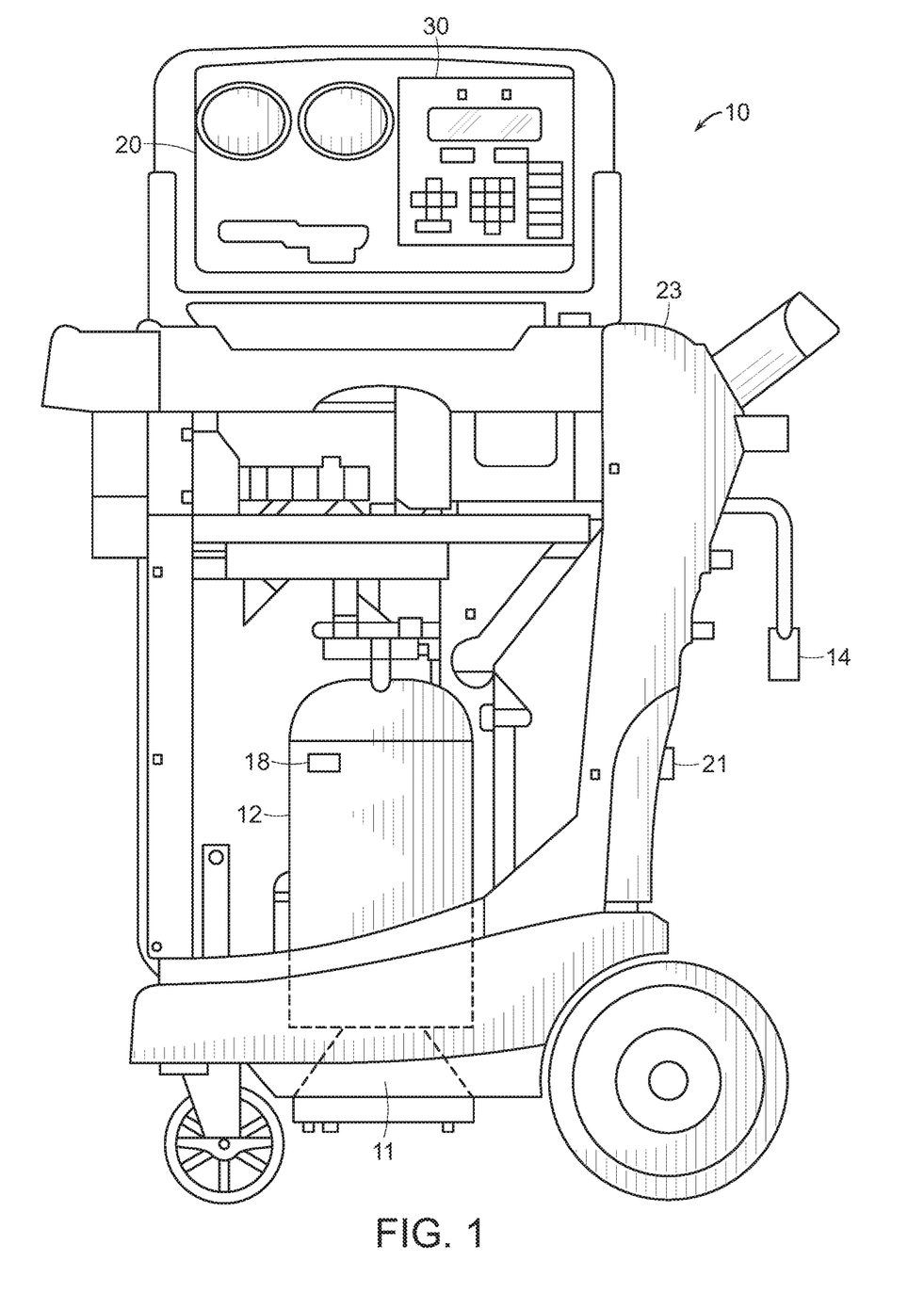
FIG. 1 is a partial cutaway front view of an air conditioning service unit.

Referring to FIG. 1, an air conditioning service ("ACS") unit 10 includes a refrigerant bottle or internal storage vessel 12, a controller 20, a housing 23, and an input/output unit 30. The housing includes an external temperature sensor 21 configured to detect an ambient temperature outside the ACS unit 10. Hose connections 14 (only one is shown in FIG. 1) protrude from the housing 23 to connect to an A/C system and facilitate transfer of refrigerant to and from the ACS unit 10.

The internal storage vessel 12 is configured to store refrigerant for the ACS unit 10. No limitations are placed on the kind of refrigerant that may be used in the ACS system.

As such, the internal storage vessel 12 is configured to accommodate any refrigerant that is desired to be collected. In some embodiments, the internal storage vessel 12 is particularly configured to accommodate refrigerants that are commonly used in the A/C systems of vehicles (e.g., cars, trucks, boats, planes, etc.), for example R-134a, $CO_2$, or R1234yf. The internal storage vessel 12 includes an internal storage vessel scale 11 configured to detect the weight of the internal storage vessel 12. The internal storage vessel further includes an internal storage vessel temperature sensor 18 configured to detect a temperature of the internal storage vessel 12. Although the temperature sensor 18 is illustrated as being placed on the outside of the internal storage vessel 12, in other embodiments the sensor 18 may be mounted inside the internal storage vessel 12. In some embodiments, the ACS unit has multiple internal storage vessels configured to store different refrigerants. In one embodiment, each independent internal storage vessel includes a separate scale and temperature sensor. In other embodiments, the independent internal storage vessels are all weighed by a single internal storage vessel scale.

Further details of the ACS system 10 are described with reference to FIG. 2, which is a schematic diagram of the ACS system 10 of FIG. 1. The ACS system 10 includes a bulkhead manifold 104, a top manifold 109, a lower manifold 107, a compressor 106, a vacuum pump 108, and an internal storage vessel assembly 120. The bulkhead manifold 104 has a high-side service hose 124 with a high-side coupler 128 and a low-side service hose 132 with a low-side coupler 136. The high-side and low-side service hoses 124, 132, respectively, are configured to attach to high-side and low-side service ports of an air conditioning system, and each of the service hoses 124, 132 are connected to a respective hose connection 14 (FIG. 1). The bulkhead manifold 104 routes the high-side service hose 124 to a high-side bulkhead hose 140 and the low-side service hose 132 to a low-side bulkhead hose 144. The high-side and low-side bulkhead hoses 140, 144 each connect the bulkhead manifold 104 to the top manifold 109.

The top manifold 109 includes a high-side inlet valve 160, which is connected to the high-side bulkhead hose 140, and a low-side inlet valve 164, which is connected to the low-side bulkhead hose 144. The inlet valves 160, 164 connect to a manifold connection tube 131 via a recovery line 171, and via a vacuum line 148. A recovery valve 172 is disposed in the recovery line 171. A first vacuum solenoid valve 168, the vacuum pump 108, and a second vacuum solenoid valve 169 are disposed in the vacuum line 148. The manifold connection tube 131 fluidly couples the top manifold 109 to the lower manifold 107.

The lower manifold 107 includes a refrigerant input conduit 130 that fluidly connects the recovery input line 131 to a receptacle such as an accumulator 138. The accumulator 138 includes a heat exchanger 184, and an accumulator pressure sensor 176 and an accumulator temperature sensor 180 configured to respectively detect the pressure and temperature in an accumulator chamber 145 defined in the accumulator 138. A compressor suction conduit 198 carries refrigerant from the accumulator 138 to the filter and dryer 142, and to a compressor suction hose 190. A compressor discharge tube 166 carries refrigerant from the compressor 106 to a compressor discharge conduit 195. The compressor discharge conduit 195 is fluidly connected to a compressor oil separator 174 via a compressor oil separator input solenoid valve 163, and also a refrigerant discharge conduit 194 via a compressor discharge solenoid valve 165. The compressor oil separator 174 is also fluidly coupled to the compressor 106 by an oil return conduit 178 and a compressor oil return hose 186. A solenoid valve 162 is disposed in the oil return conduit 178, and can be controlled to selectively drain the oil from the oil separator 174 to the compressor 106. Vapor refrigerant from the compressor oil separator 174 is carried through the vapor refrigerant return conduit 173 to the heat exchanger 184. The refrigerant discharge conduit 194 fluidly connects the compressor heat exchanger 184 (and the compressor discharge conduit 195 via the separator input solenoid valve 163) to a refrigerant discharge hose 115.

The refrigerant discharge hose 115 delivers the refrigerant vapor from the lower manifold 107 to the internal storage vessel assembly 120. The internal storage vessel assembly 120 includes the internal storage vessel 12 having the internal storage vessel assembly temperature sensor 18 and the internal storage vessel scale 11.

Figure 3:
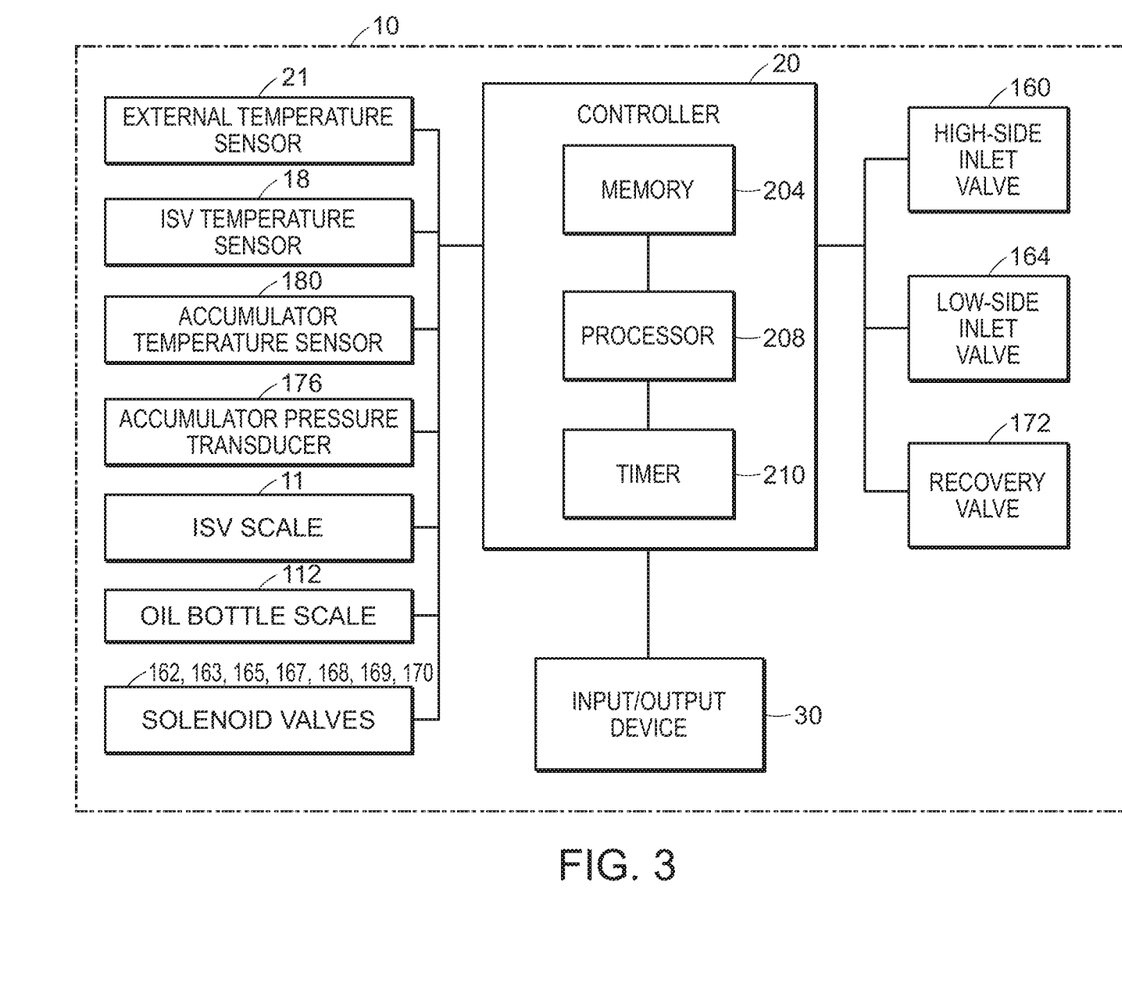
FIG. 3 is a schematic view of the control components of the air conditioning service unit of FIG. 1.

FIG. 3 is a schematic diagram of the controller 20 and the components communicating with the controller 20 in the ACS system 10. Operation and control of the various components and functions of the ACS system 10 are performed with the aid of the controller 20. The controller 20 is implemented with a general or specialized programmable processor 208 that executes programmed instructions. In some embodiments, the controller includes more than one general or specialized programmable processor. The instructions and data required to perform the programmed functions are stored in a memory unit 204 associated with the controller 20. The controller 20 also includes a timer 210. The processor 208, memory 204, timer 210 and interface circuitry configure the controller 20 to perform the functions described above and the processes described below. These components can be provided on a printed circuit card or provided as a circuit in an application specific integrated circuit (ASIC). Each of the circuits can be implemented with a separate processor or multiple circuits can be implemented on the same processor. Alternatively, the circuits can be implemented with discrete components or circuits provided in VLSI circuits. Also, the circuits described herein can be implemented with a combination of processors, ASICs, discrete components, or VLSI circuits.

The external temperature sensor 21, internal storage vessel temperature sensor 18, and accumulator temperature sensor 180 are configured to transmit electronic signals representing the respective detected temperatures to the controller 20. The accumulator pressure transducer 176 transmits electronic signals representing the detected pressure in the accumulator 138 to the controller 20. In addition, the internal storage vessel scale 11 transmits electronic signals representing the detected weight of the internal storage vessel 12 to the controller 20, and an oil bottle scale 112 transmits electronic signals representing the detected weight of the accumulator 138 to the controller 20. The controller 20 includes the timer 210 so that the time at which each sensor signal is received can be determined and recorded. In various different embodiments, the ACS unit 10 does not include all of the sensors 21, 18, 180, 176, and 11. In such embodiments, the ACS unit 10 can be configured with any desired combination of an external temperature sensor 21, the internal storage vessel temperature sensor 18, an accumulator temperature sensor 180, an accumulator pressure transducer 176, and the internal storage vessel scale 11.

The controller 20 is electrically connected to and configured to receive the temperature signals from the temperature sensors 18, 21, and 180, receive the pressure signal from the pressure transducer 176, receive the internal storage vessel weight signal from the internal storage vessel scale 11, and receive the oil bottle weight signal from the oil bottle scale 112. The signals from the sensors and transducers are transmitted when requested by the controller 20 or are sent continuously or on a predetermined basis, such as every second, 5 seconds, 10 seconds, 30 seconds, minute, 5 minutes, 15 minutes, 30 minutes, hour, etc.

The signals indicating pressure, temperature and time received by the controller 20 are stored in the memory 204 of the controller 20. The processor 208 transmits signals to operate the high-side inlet valve 160, the low-side inlet valve 164, the recovery valve 172, and the solenoid valves 162, 163, 165, 168, 169, 170 based on the sensor signals and control algorithms stored in the memory 204 of the controller 20. The controller is also connected to the input/output device 30 to enable a user to input parameters and activate operating algorithms for the controller 20, and to enable the controller to display information to the user of the ACS unit 10.

Figure 2:
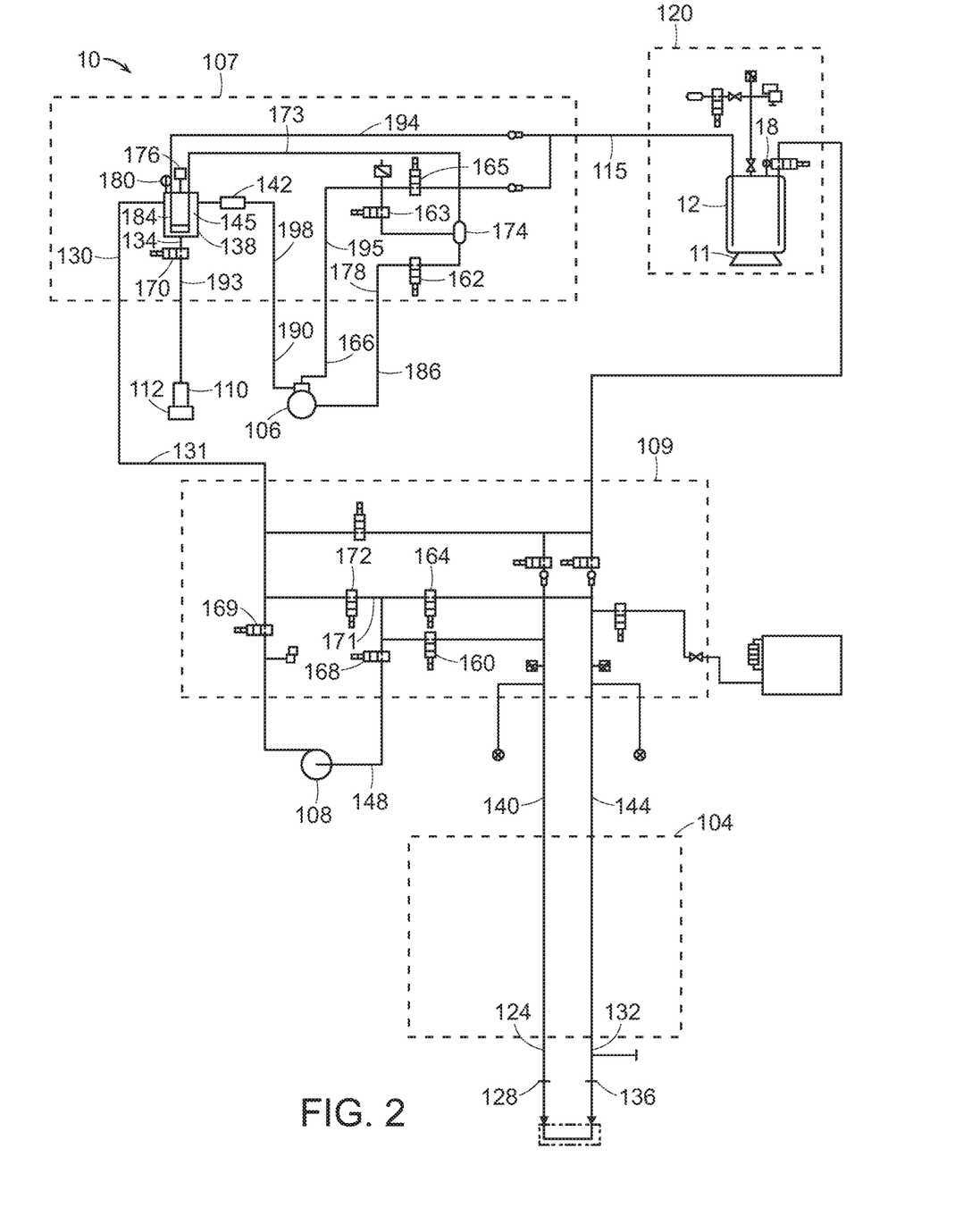
FIG. 2 is a schematic view of the air conditioning service unit of FIG. 1.

Referring to FIG. 2, in operation, the high-side and low-side couplers 128, 136 are connected to the high-side and low-side connection ports of an air conditioning system. The high-side and low-side solenoids 160, 164 and the recovery solenoid 172 are opened to perform a recovery operation, enabling compressed refrigerant within the air conditioning system to flow to the lower manifold 107. The refrigerant enters the accumulator 138 via the refrigerant input conduit 130, where heat from the compressor oil separator 174 vaporizes the refrigerant. A small amount of system oil is typically entrained in the refrigerant during normal use in the air conditioning system. The system oil has a higher boiling point than the refrigerant, and therefore remains in a liquid phase and falls to the bottom of the accumulator 138 under the force of gravity as the refrigerant is vaporized.

The controller 20 controls the compressor oil separator input solenoid valve 163 and activates the compressor 106 to generate a negative pressure in the compressor suction hose 190 and compressor suction conduit 198 to pull the vaporized refrigerant in the accumulator chamber 145 through the filter and dryer unit 142. The filter and dryer unit 142 removes moisture and other contaminants present in the refrigerant. The refrigerant continues through the compressor suction conduit 198 and the compressor suction hose 190 into the compressor 106. The compressor 106 pressurizes the refrigerant and forces the refrigerant through the compressor discharge tube 166 and into the compressor discharge conduit 195. During the pass through the compressor 106, the temperature of the refrigerant increases substantially, such that the refrigerant in the compressor discharge conduit 195 is hotter than the refrigerant coming into the system.

The heated and pressurized refrigerant passes through the opened valve 163, and into the compressor oil separator 174. A coalescing filter (not shown) of the compressor oil separator 174 separates the refrigerant from any oil that may have been entrained in the refrigerant during the pass through the compressor 106. The refrigerant vapor enters the heat exchanger 184 through the vapor refrigerant return conduit 173. The refrigerant vapor in the heat exchanger 184 in turn transfers heat to the refrigerant and oil in the accumulator chamber 145 to assist in vaporizing the refrigerant entering the accumulator 138. The vapor refrigerant then enters the discharge conduit 194 and exits the lower manifold 107 through the refrigerant discharge hose 115 to be stored in the internal storage vessel 12, or to be returned to the air conditioning system.

In order to facilitate optimal performance of the air conditioning system, it is necessary to accurately replace the oil and refrigerant recovered from the air conditioning system during the recovery process. Thus, it is necessary to accurately a) determine the amount of refrigerant recovered in the internal storage vessel 12 during the recovery process; b) determine the amount of oil that was recovered in the oil recovery bottle 110 during the recovery process; and c) to determine the amount of refrigerant that was dissolved in the recovered oil. By determining the amount of refrigerant that was dissolved in the recovered oil, both the amount of refrigerant and oil to be replaced in the air conditioning system can be more accurately calculated.

As previously discussed, the recovered refrigerant is stored in the internal storage vessel 12 of the ACS unit 10. The internal storage vessel 12 is weighed before and after the recovery process to determine the amount of refrigerant that was recovered $A_{rm}$.

The system oil that remains in a liquid phase and has fallen to the bottom of the accumulator 138 is drained from the accumulator chamber 145 via an oil drain outlet 134 that is controlled by a solenoid outlet valve 170. The drained oil is collected in an oil bottle 110. The oil bottle 110 is weighed before and after the recovery process to determine the measured amount of oil that was recovered $A_{om}$.

It is possible to estimate the amount of refrigerant that was dissolved in the drained oil $A_{rd}$ based on parameters such as amount of oil drained from the accumulator 138 and the time t required to drain the oil from the accumulator 138. In addition, the type of oil used in the air conditioning unit and the ambient temperature T affect the amount of refrigerant that gets dissolved in oil, and must be taken into account.

Based on these parameters, experimental data was used to create an equation that defines the relationship between a ratio R of the amount of dissolved refrigerant in the recovered oil Air to the measured amount of recovered oil $A_{om}$ (e.g., $R=A_{rd}/A_{om}$) and a rate of oil drain r. The relationship was experimentally determined based on three different, commonly used oils and on three different ambient temperatures. Since the values for the measured amount of oil recovered $A_{om}$ and the rate of oil drain r are easily measured during a recovery process using the ACS unit 10, the relationship can be used to calculate the amount of dissolved refrigerant in the recovered oil $A_{rd}$. For example, $$A_{rd}=A_{om}*R.$$

Experimental data obtained at three different temperatures and for three refrigerants was used to create an equation E(T) that defines a relationship between the ratio R and the rate of oil drain for a given temperature T. The experimental procedure used to determine the equation E(T) that defines the relationship between the ratio R and the rate of oil drain for a given temperature will now be described.

A known amount of refrigerant and a known amount of oil were mixed in a bottle by shaking to provide a control sample of refrigerant that includes entrained oil such as would be obtained by the ACS unit 10 during a recovery procedure. The bottle was connected to the ACS unit 10 and a recovery procedure was performed as described above, whereby refrigerant and oil were collected in the accumulator 138. Recovered refrigerant was transferred to the internal storage vessel 12 and oil that accumulated in the accumulator 138 was drained to the oil bottle 110. The amount of oil recovered $A_{om}$ in the oil bottle 110 was measured using the oil bottle scale 112, and the time for oil drain t was calculated based on a difference between a drain start time and a drain stop time. The ambient temperature was controlled and thus known, and the rate of oil drain r was obtained by dividing the amount of oil recovered $A_{om}$ in the oil bottle 110 by the time to drain t. The recovered oil was then heated and stirred, whereby any refrigerant that had been dissolved in the recovered oil was removed from the recovered oil. Following the heating and stirring procedure, the weight of the recovered oil was measured again. The difference between the weight of the recovered oil before heating and stirring and the weight of the recovered oil after heating and stirring, which corresponds to the amount of refrigerant dissolved in the recovered oil $A_{rd}$, was calculated. The ratio R of the amount of dissolved refrigerant in the recovered oil $A_{rd}$ to the measured amount of recovered oil $A_{om}$ was then calculated.

Figure 4:
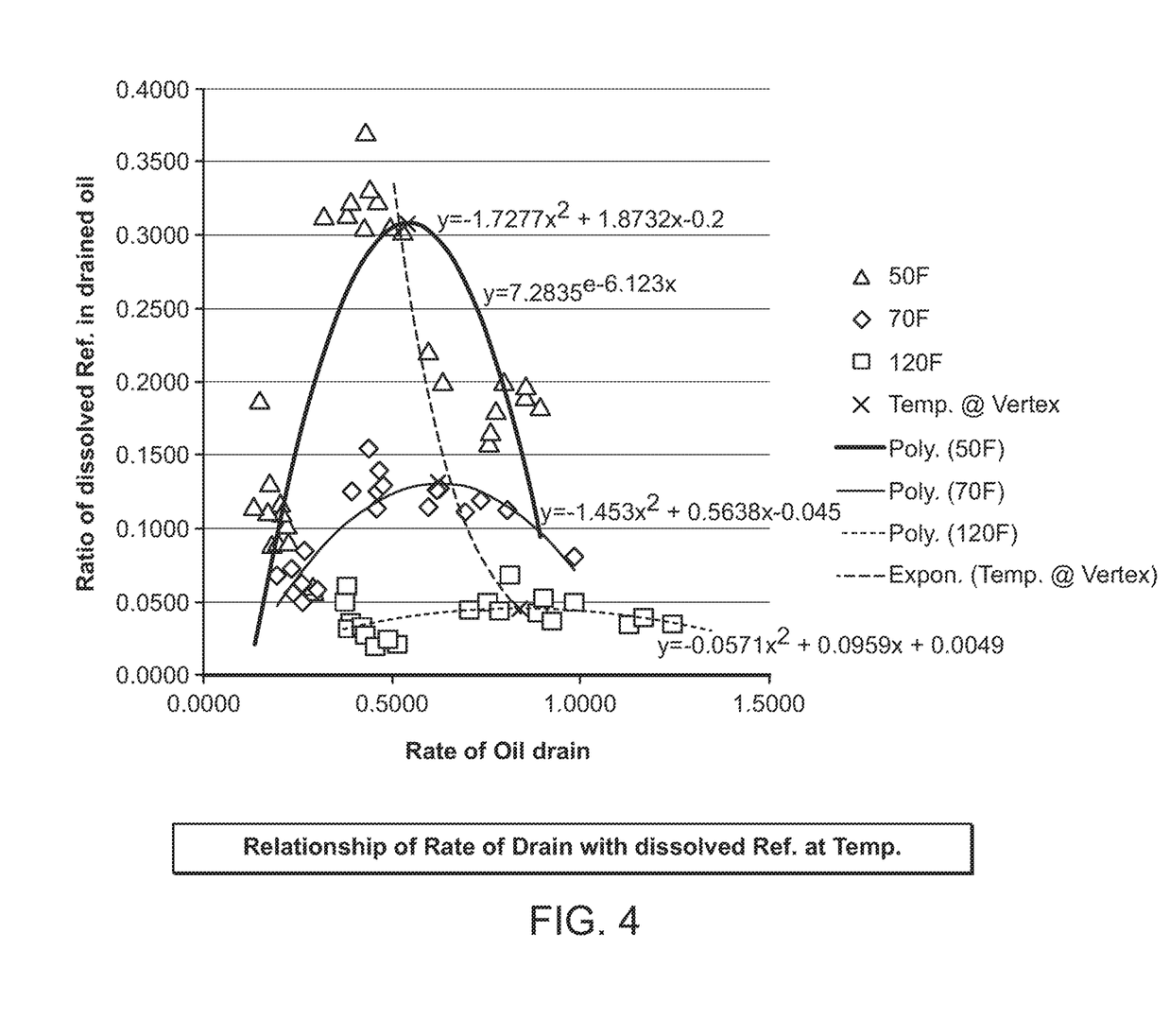
FIG. 4 is a graph of the rate of oil drain versus the ratio of the amount of dissolved refrigerant to the amount of recovered oil.

This procedure was repeated using different types of compressor oil at different ambient temperatures T. In addition, for a given compressor oil and ambient temperature T, the amounts of oil entrained into the refrigerant were varied. For the various ambient temperatures T used in the tests, the ratio R and the rate of drain were determined. Numerical methods were applied to the experimental data using software to identify a second order (e.g., parabolic) equation E(T) describing the relationship between the rate of drain r and the ratio R for a given temperature. The experimental data and parabolic equations are illustrated in FIG. 4 for ambient temperatures of 50 degrees Fahrenheit (10 degrees Celsius), 70 degrees Fahrenheit (21 degrees Celsius) and 120 degrees Fahrenheit (49 degrees Celsius). The equation E(T) for a given ambient temperature T was found to be $$R=a(r-h)^2+k$$

In the equation E (T), the constants a, h and k are determined experimentally. As shown in FIG. 6, for a temperature of 50 degrees Fahrenheit (10 degrees Celsius), the equation E(50) is $$R=(-1.7277)(r-0.5421)^2+0.3073.$$

In addition, for a temperature of 70 degrees Fahrenheit (21 degrees Celsius), the equation E(70) is $$R=(-0.453)(r-0.6223)^2+0.1307,$$

and for a temperature of 120 degrees Fahrenheit (49 degrees Celsius), the equation E(120) is $$R=(-0.0571)(r-0.839)^2+0.0453.$$

Thus, for a given rate of drain of an oil recovered by the ACS unit 10, the ratio R can be calculated. Once the ratio is known, the relationship $A_{rd}=A_{om}*R$ can be used to calculate the amount of dissolved refrigerant in the recovered oil $A_{rd}$.

In some embodiments, the ratio R may be determined for temperatures intermediate those shown in the graph of FIG. 6 by interpolation, while in other embodiments, additional experimental data may be obtained for a given intermediate temperature and used to generate an equation E(T) for that temperature.

The amount of dissolved refrigerant in the recovered oil $A_{rd}$ can be used as a correction factor. That is, by removing the amount of dissolved refrigerant in the recovered oil $A_{rd}$ from the measured amount of recovered oil $A_{om}$, the accuracy of the amount of recovered oil $A_{om}$ can be improved.

In addition, by adding the amount of dissolved refrigerant in the recovered oil $A_{rd}$ to the measured amount of recovered refrigerant $A_{rm}$, the accuracy of the amount of recovered refrigerant can be improved.

Figure 5:
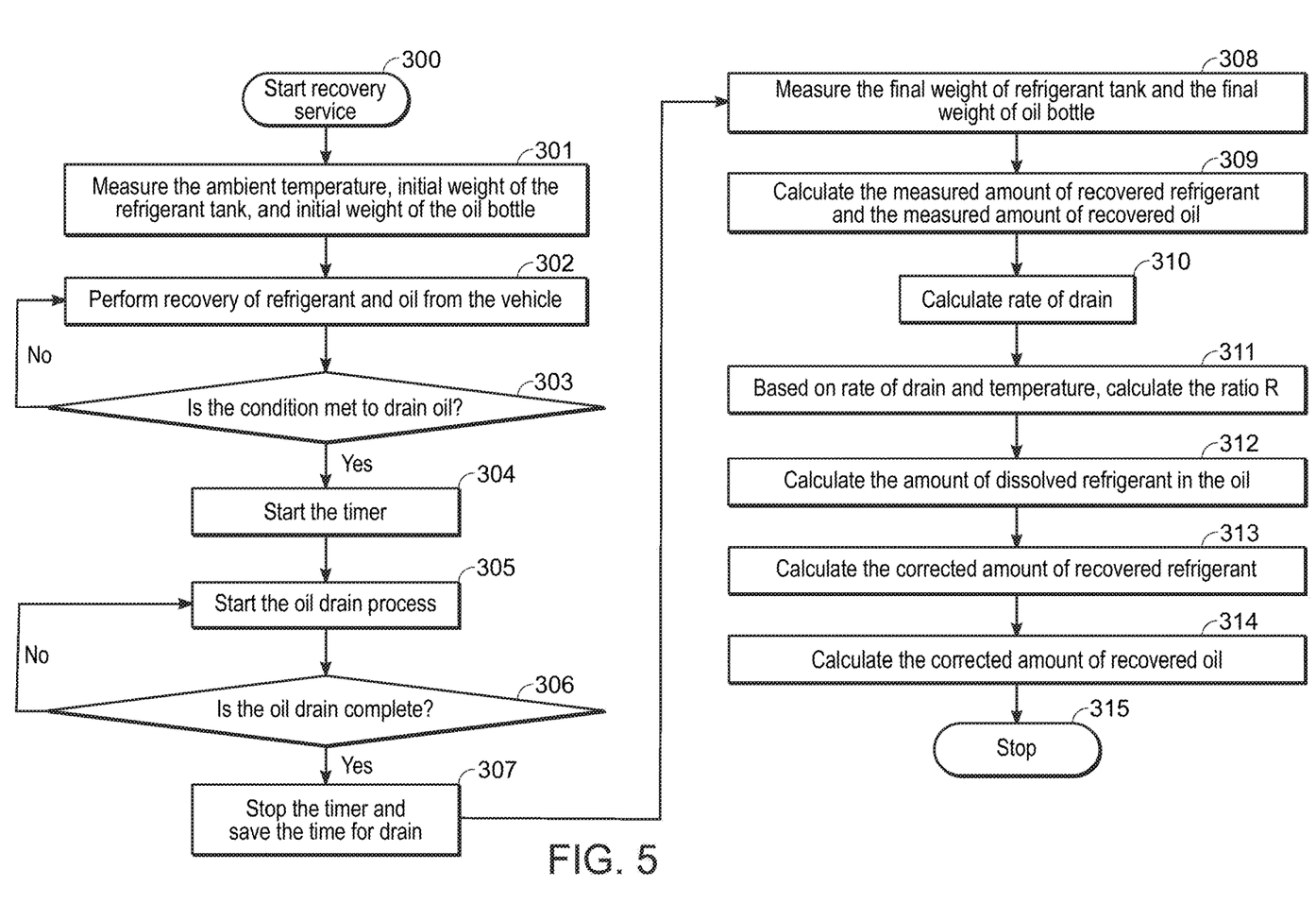
FIG. 5 is a process diagram of a method for operating a controller of the an air conditioning service unit of FIGS. 1-3 to calculate the corrected amount of refrigerant recovered and the corrected amount of oil recovered.

Referring to FIG. 5, a method of determining an amount of oil in a refrigerant-oil mixture recovered from an air conditioning unit can be implemented in the ACS 10 to accurately determine the amount of recovered refrigerant and the amount of recovered oil by correcting measured amounts to account for refrigerant that has been dissolved in the entrained oil. The method includes the following method steps:

In an initial step (step 300), the recovery service is started. At the time of starting the recovery service and before any refrigerant is recovered from the air conditioning system, several measurements are made. In particular, the ambient temperature T is measured using the external temperature sensor 21, the initial weight $W_{ISVi}$ of the internal storage vessel 12 used to receive the recovered refrigerant is determined using the internal storage vessel scale 11, and the initial weight $W_{OBi}$ of the oil bottle 110 used to receive the recovered oil is determined by using the oil bottle scale 112 (step 301).

Once the initial measurements are made, the ACS 10 is operated normally to recover the refrigerant as described above (step 302). The controller 20 periodically checks to see whether refrigerant recovery is complete, for example by monitoring parameters such as the elapsed time, the accumulator pressure as indicated by accumulator pressure sensor 176, etc., or a combination of such parameters (step 303).

Once the controller 20 determines that all fluid has been recovered from the air conditioning system, the controller 20 initiates a drain timer (step 304) and opens the oil drain outlet valve 170 (step 305), allowing oil captured in the accumulator 138 to drain to the oil bottle 110. The draining step 305 continues until oil no longer remains in the accumulator 138. The controller 20 periodically checks to see whether the oil drain is complete, for example by monitoring parameters such as elapsed time, accumulator pressure as indicated by accumulator pressure sensor 176, etc. or a combination of such parameters (step 306).

When the oil has been completely drained from the accumulator 138 to the oil bottle 110, the controller 20 stops the drain timer, and determines the amount of time t that was required to drain the oil from the accumulator 138 (referred to hereafter as "time for oil drain t"). In addition, the time for oil drain t is saved in the memory 204 of the controller 20 (step 307).

Once the time for oil drain t has been saved, the final weight $W_{ISVf}$ of the internal storage vessel 12 used to receive the recovered refrigerant is determined using the internal storage vessel scale 11, and the final weight $W_{OBf}$ of the oil bottle 110 used to receive the recovered oil is determined by using the oil bottle scale 112 (step 308). The measured amount of recovered refrigerant $A_{rm}$ is determined by calculating the difference between the final weight $W_{ISVf}$ of the internal storage vessel 12 and the initial weight $W_{ISVi}$ of the internal storage vessel 12. In addition, the measured amount of recovered oil $A_{om}$ is determined by calculating the difference between the final weight $W_{OBf}$ of the oil bottle 110 and the initial weight $W_{OBi}$ of the oil bottle 110 (Step 309).

Based on the time for oil drain t and the measured amount of recovered oil $A_{om}$, the rate of oil drain r is calculated, for example, $$r=A_{om}/t.$$

For a given ambient temperature T, the rate of oil drain r from the accumulator 138 to the oil bottle 110 is entered into the equation E(T) in order to calculate the ratio R of the amount of dissolved refrigerant in the recovered oil $A_{rd}$ to the amount of recovered oil $A_{om}$ (step 311). Once the ratio R has been calculated, the ratio R can be used to calculate the amount of dissolved refrigerant in the recovered oil $A_{rd}$, for example by multiplying the calculated ratio R by the measured amount of recovered oil $A_{om}$ as follows: $A_{rd}=A_{om}*R$ (step 312).

The corrected amount of refrigerant recovered $A_{rd}$ is then calculated by adding the amount of dissolved refrigerant in the recovered oil $A_{rd}$ to the measured amount of recovered refrigerant $A_{rm}$ (step 313):

$$A_{rc}=A_{rm}+A_{rd}$$

In addition, the corrected amount of oil recovered $A_{oc}$ is then calculated by subtracting the amount of dissolved refrigerant in the recovered oil $A_{rd}$ from the measured amount of recovered oil $A_{om}$ (step 314):

$$A_{oc}=A_{om}-A_{rd}$$

Thus, the ACS unit 10 determines the corrected amount of refrigerant recovered $A_{rc}$ and the corrected amount of oil recovered $A_{oc}$ and provides this information to the unit operator via, for example, the input/output unit 30 of the ACS unit 10 and/or other conventional methods for communicating information (step 315). This information can be used to ensure that proper amounts of refrigerant and oil are used when recharging the air conditioning system with refrigerant and the air conditioning system compressor with oil. The method may include a recharging step in which the air conditioning system is recharged with the corrected amount of refrigerant recovered $A_{rd}$ and the corrected amount of oil recovered $A_{oc}$. In some embodiments, the recharging step may be performed by the ACS unit 10. In other embodiments, the recharging step may be performed manually, for example by an operator of the ACS unit 10.

In the illustrated embodiment, the measured amount of recovered oil was determined by calculating a difference in weight of the oil bottle 110 before and after the recovered oil was transferred there. However, determination of the measured amount of recovered oil can be accomplished in many ways. For example, pressure measurements can be used to determine the volume of oil that was drained. In this example, the ACS unit 10 is configured to drain the oil removed from the refrigerant accumulated in the chamber 145 of the accumulator 138 while measuring the change in pressure of the vapor refrigerant in the chamber 145 over time. The pressure measurements can be used to determine the volume of oil that was drained, as described in co-pending U.S. patent application Ser. No. 14/964,822, filed on 10 Dec. 2015.

It will be appreciated that variants of the above-described and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the foregoing disclosure.

What is claimed is:

1. An air conditioning service unit comprising,
a receptacle configured to receive a refrigerant-oil mixture recovered from an air conditioning system, the receptacle including a drain valve;
a refrigerant vessel including a first load transducer configured to determine a weight of the refrigerant vessel;
an oil drain bottle including a second load transducer configured to determine a weight of the oil drain bottle;
a tinier;
a temperature sensor configured to detect an ambient temperature of the system; and
a controller configured to receive as inputs information sent from the temperature sensor, the first load transducer, the second load transducer and the timer, the controller including a processor configured to execute instructions stored in a memory to determine an amount of oil in the refrigerant-oil mixture recovered from the air conditioning unit and collected in the receptacle, by
collecting the refrigerant-oil mixture recovered from the air conditioning system in the receptacle;
draining from the receptacle oil that separated from the refrigerant-oil mixture;
measuring an amount of the oil drained from the receptacle to obtain a measured amount of recovered oil; and
calculating a corrected amount of recovered oil in the refrigerant-oil mixture by correcting the measured amount of recovered oil to account for an amount of dissolved refrigerant in the recovered oil.

2. The air conditioning service unit of claim 1, wherein the processor is further configured to determine an amount of oil in the refrigerant-oil mixture recovered from the air conditioning unit by:
prior to draining oil from the receptacle to the oil drain bottle, detecting an initial weight, of the oil drain bottle based on output from the second transducer;
detecting an ambient temperature based on output from the temperature sensor;
draining the oil from the receptacle to the oil drain bottle, including
starting the tinier and storing a timer start time;
opening the drain valve to drain from the receptacle oil that has separated from the refrigerant-oil mixture disposed in the receptacle;
detecting if the oil has been drained from the receptacle;
stopping the timer when it has been determined that the oil has been drained from the receptacle and storing a timer stop time;
calculating a time required for draining the oil from the receptacle into the oil drain bottle by determining a difference between the timer stop time and the time start time;
following transferring oil from the receptacle to the oil drain bottle, detecting a final weight of the oil drain bottle based on output from the second transducer;
calculating a difference between the final weight of the oil drain bottle and the initial weight of the oil drain bottle to provide a measured amount of recovered oil;
calculating an amount of dissolved refrigerant in the recovered oil,
calculating a corrected amount of oil in the refrigerant-oil mixture by correcting the measured amount of recovered oil to account for the amount of dissolved refrigerant in the recovered oil.

3. The air conditioning service unit of claim 1, wherein the processor is further configured to determine an amount of refrigerant that is dissolved in the measured amount of recovered oil by:
calculating a rate of oil drain by dividing the measured amount of recovered oil by a time required to drain oil from the receptacle;
detecting an ambient temperature;
determining a ratio R of the amount of dissolved refrigerant in the recovered oil to the measured amount of recovered oil;

and calculating the amount of dissolved refrigerant in the recovered oil by multiplying the value calculated for R by the measured amount of recovered oil.

4. The air conditioning service unit of claim 1, wherein the processor is configured to execute instructions stored in a memory to determine an amount of refrigerant in the refrigerant-oil mixture recovered from the air conditioning unit and collected in the receptacle, by prior to transferring refrigerant from the receptacle to the refrigerant vessel, detecting an initial weight of the refrigerant vessel based on output from the first load transducer;

transferring from the receptacle to the refrigerant vessel refrigerant separated from the refrigerant-oil mixture disposed in the receptacle;

following transfer of refrigerant from the receptacle to the refrigerant vessel, detecting a finial weight of the refrigerant vessel based on output from the first load transducer;

calculating a difference between the final weight of the refrigerant vessel and the initial weight of the refrigerant vessel to provide a measured amount of recovered refrigerant corresponding to an amount of the refrigerant transferred from the receptacle; and calculating a corrected amount of recovered refrigerant by correcting the measured amount of recovered refrigerant to account for an amount of dissolved refrigerant in the recovered oil.

5. The air conditioning service unit of claim 4, wherein the processor is configured to execute instructions stored in a memory to recharge an air conditioning system with an amount of refrigerant corresponding to the corrected amount of recovered refrigerant.

6. The air conditioning service unit of claim 1, wherein the processor is configured to execute instructions stored in a memory to recharge an air conditioning system with an amount of oil corresponding to the corrected amount of recovered oil.

* * * * *

UNITED STATES PATENT AND TRADEMARK OFFICE
CERTIFICATE OF CORRECTION

PATENT NO. : 10,627,142 B2
APPLICATION NO. : 15/685923
DATED : April 21, 2020
INVENTOR(S) : William Brown, Mark McMasters and Mahendra Hospet Basavapura Srinivasa Page 1 of 1

It is certified that error appears in the above-identified patent and that said Letters Patent is hereby corrected as shown below:

In the Claims

In Claim 1, at Column 13, Line 62, delete the word "tinier" and insert the word --timer-- in its place.

In Claim 2, at Column 14, Line 23, delete the "," between the words "weight" and "of".

In Claim 2, at Column 14, Line 29, delete the word "tinier" and insert the word --timer-- in its place.

In Claim 2, at Column 14, Lines 40-41, delete the phrase "time start time" and insert the phrase --timer start time-- in its place.

Signed and Sealed this
Twenty-fourth Day of November, 2020

Andrei Iancu
*Director of the United States Patent and Trademark Office*